(12) United States Patent
Lowe et al.

(10) Patent No.: US 7,268,271 B2
(45) Date of Patent: Sep. 11, 2007

(54) METHODS OF USE OF LEC1 POLYNUCLEOTIDES AND POLYPEPTIDES

(75) Inventors: Keith S. Lowe, Johnston, IA (US); William J. Gordon-Kamm, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 209 days.

(21) Appl. No.: 10/199,609

(22) Filed: Jul. 19, 2002

(65) Prior Publication Data

US 2004/0016022 A1 Jan. 22, 2004

(51) Int. Cl.
*C12N 15/82* (2006.01)
*A01H 5/00* (2006.01)

(52) U.S. Cl. ........................ 800/290; 800/298

(58) Field of Classification Search ................ 435/419, 435/468; 800/290, 298, 320–320.3, 312, 800/322, 306, 314
See application file for complete search history.

(56) References Cited

U.S. PATENT DOCUMENTS

| 5,811,636 | A | 9/1998 | Hanna et al. | |
|---|---|---|---|---|
| 6,235,975 | B1 | 5/2001 | Harada et al. | |
| 6,320,102 | B1 | 11/2001 | Harada et al. | |
| 6,781,035 | B1 * | 8/2004 | Harada et al. | 800/290 |

FOREIGN PATENT DOCUMENTS

| WO | WO98/37184 A1 | 8/1998 |
|---|---|---|
| WO | WO99/67405 A2 | 12/1999 |

OTHER PUBLICATIONS

Rhoads D.M. et al. Regulation of the cyanide-resistant alternative oxidase of plant mitochondria. Identification of the cysteine residue involved in alpha-keto acid stimulation and intersubunit dislfide bond . . . J Biol Chem. Nov. 13, 1998;273(46):30750-6.*
Harada et al. Sequence 19, U.S. Appl. No. 09/516,052, current filing date Mar. 2, 2001, alignment with SEQ ID No. 1.*
Bellorini et al., CCAAT binding NF-Y-TBP interactions: NF-YB and NF-YC require short domains adjacent to their histone fold motifs for association with TBP basic residues, Nucleic Acids Research 25(11):2174-2181 (1997).
Edwards et al., Multiple Genes Encoding the Conserved CCAAT-Box Transcription Factor Complex Are Expressed in Arabidopsis, Plant Physiol. 117:1015-1022 (1998).
Lotan et al., Arabidopsis LEAFY COTYLEDON1 Is Sufficient to Induce Embryo Development in Vegetative Cells, Cell 93:1195-1205 (1998).
Sasaki, T., Accession No. C19737, Rice EST, EBI Database (1996).
Sasaki, T., Accession No. C28028, Rice EST, EBI Database (1997).
West et al., LEAFY COTLEDON1 is an Essential Regulator of Late Embryogenesis and Cotyledon Identify in Arabidopsis, Plant Cell 6:1731-1745 (1994).
Parcy et al., The ABSCISIC ACID-INSENSITIVE3, FUSCA3 and LEAFY COTYLEDON1 Loci Act in Concert to Control Multiple Aspects of Arabidopsis Seed Development, Plant Cell 9:1265-1277 (1997).
Ohad et al., A mutation that allows endosperm development without fetrtilization, Proc. Natl. Acad. Sci. USA 93:5319-5324 (1996).
Shoemaker et al., Accession No. AI495007, Soybean EST, EBI Database (1999).
Li et al., Accession No. X59714, CAAT-box DNA binding protein, NCBI Database (1992).
Bork, P., Powers and Pitfalls in Sequence Analysis: The 70% Hurdle, Genome Research 10:398-400 (2000).
Lazar et al., Transforming Growth Factor Alpha: Mutation of Aspartic Acid 47 and Leucine 48 Results in Different Biological Activities, Molecular and Cellular Biology 8(3):1247-1252 (1988).
Sequence Search Result Accession No. Y11210 (1997).
Broun et al., Catalytic Plasticity of Fatty Acid Modification Enzymes Underlying Chemical Diversity of Plant Lipids, Science 282:1315-1317 (1998).
Kemp et al., Accession No. AAN60472 (1991).
Yu et al., A Draft Sequence of the Rice Genome (Oryza sativa L. ssp. indica), Science 296:79-92 (2002).

* cited by examiner

*Primary Examiner*—Cynthia Collins

(57) ABSTRACT

The invention provides novel uses for isolated LEC1 nucleic acids and their encoded proteins. The proteins are transcriptional activators. The invention further provides expression cassettes, transformed host cells, and transgenic plants and plant parts.

7 Claims, No Drawings

METHODS OF USE OF LEC1 POLYNUCLEOTIDES AND POLYPEPTIDES

TECHNICAL FIELD

The present invention relates generally to plant molecular biology. More specifically, it relates to methods for using LEC1 polynucleotide in plants.

BACKGROUND OF THE INVENTION

Major advances in plant transformation have occurred over the last few years. However, in major crop plants, such as maize and soybeans, serious genotype limitations still exist. Transformation of agronomically important rice cultivars (and a small number of maize inbreds) has reached workable levels using either particle bombardment or *Agrobacterium* to deliver DNA. However, losses in efficiency occur due to reductions in embryogenecity and subsequent regeneration. Traditionally, embryogenecity and regeneration were improved by optimizing medium components and/or explant material and source. This led to success, but improvements are still needed to make the process more efficient and less time consuming. Therefore it would be desirable to provide improved methods capable of increasing transformation efficiency, stimulating embryogenic growth in culture and improving regeneration of vigorous, fertile plants.

DETAILED DESCRIPTION OF THE INVENTION

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "nucleic acid" and "polynucleotide" are used interchangeably and mean polynucleotides including single or double-stranded polymer of deoxyribonucleotide or ribonucleotide bases. Also included are polynucleotide fragments and variants. Nucleic acids may also include modified nucleotides.

As used herein, "LEC1 nucleic acid" means a nucleic acid or polynucleotide that codes for a LEC1 polypeptide.

As used herein, "polypeptide" and "protein" are used interchangeably and mean proteins, protein fragments, modified proteins, amino acid sequences and synthetic amino acid sequences. The polypeptide can be glycosylated or not.

As used herein, "LEC1 polypeptide" means a HAP3 family member transcriptional activator polypeptide that regulates gene expression during embryo development.

As used herein, "plant" includes plants and plant parts including but not limited to plant cells, plant tissue such as leaves, stems, roots, flowers, and seeds.

As used herein, "promoter" includes reference to a region of DNA upstream from the start of transcription and involved in recognition and binding of RNA polymerase and other proteins to initiate transcription.

By "fragment" or "subsequence" is intended a portion of the nucleotide sequence or a portion of the amino acid sequence. Fragments of a nucleotide sequence may encode protein fragments that retain the biological activity of the native nucleic acid. Alternatively, fragments of a nucleotide sequence that are useful as hybridization probes or as antisense polynucleotides generally do not encode fragment proteins retaining biological activity. Thus, fragments of a nucleotide sequence are generally greater than 20, 30, 50, 100, 150, 200, 300, 400, or 500 nucleotides and up to the entire nucleotide sequence encoding the proteins of the invention. Generally the probes are less than 1000 nucleotides and often less than 500 nucleotides. Fragments of the invention include antisense sequences used to decrease expression of the inventive polynucleotides. Such antisense fragments may vary in length ranging from at least about 20 nucleotides, at least about 50 nucleotides, at least about 100 nucleotides, and up to and including the entire coding sequence.

By "functional equivalent" as applied to a polynucleotide or a protein is intended a polynucleotide or a protein of sufficient length to modulate the level of LEC1 protein activity in a plant cell. A polynucleotide functional equivalent can be in sense or antisense orientation.

By "variants" is intended substantially similar sequences. Generally, nucleic acid sequence variants of the invention will have at least about 60%, 65%, 70%, 75%, 80% 90%, 95%, or at least 98% sequence identity to the native nucleotide sequence, wherein the % sequence identity is based on the entire sequence and is determined by GAP analysis using Gap Weight of 50 and Length Weight of 3. Generally, polypeptide sequence variants of the invention will have at least about 50%, 55%, 60%, 65%, 70%, 75%, 80%, 85%, 90%, 95%, or at least 98% sequence identity to the native protein, wherein the % sequence identity is based on the entire sequence and is determined by GAP analysis using Gap Weight of 12 and Length Weight of 4.

As used herein "Stable Transformation" refers to the transfer of a nucleic acid fragment into a genome of a host organism (this includes both nuclear and organelle genomes) resulting in genetically stable inheritance. In addition to traditional methods, stable transformation includes the alteration of gene expression by any means including chimerplasty or transposon insertion.

As used herein "Transient Transformation" refers to the transfer of a nucleic acid fragment into the nucleus (or DNA-containing organelle) of a host organism resulting in gene expression without integration and stable inheritance.

As used herein "Modified cells" are cells that have been transformed.

As used herein "Re-transformation" refers to the transformation of a modified cell.

Nucleic Acids

The present invention relates to HAP3-type transcriptional activator polynucleotides and polypeptides, and in particular leafy cotyledon 1 transcriptional activator (LEC1) polynucleotides and polypeptides. In other aspects the present invention relates to expression cassettes, host cells transfected with at least one expression cassette, and transgenic plants and seeds comprising the expression cassettes. Further aspects of the invention include methods of using the polynucleotides and polypeptides. Such methods include methods of modulating expression of the polynucleotides in a plant. Expression of the polynucleotides can be increased or decreased relative to a non-transformed control plant. In another aspect, the present invention relates to modulating the level and/or activity of the LEC1 polypeptides. Also provided are methods for increasing transformation efficiency, enhancing tissue culture response, inducing somatic embryogenesis, providing a method for positive selection, and/or producing a somatic embryo by apomixis means. The methods comprise introducing a LEC1 nucleic acid into the plant cell to produce a plant cell that exhibits altered LEC1 activity.

Expression of the LEC1 polynucleotide initiates formation of embryo-like structures and improves growth and recovery of transformants. It is expected that LEC1 polynucleotides will induce apomixis. The term apomixis is used to describe asexual reproduction that replaces or substitutes sexual methods of reproduction. When apomixis occurs, embryos are produced from maternal tissue and use only the maternal genome. In many cases of apomixis maternal tissues such as the nucellus or inner integument "bud off" producing somatic embryos. These embryos then develop normally into seed. Since meiosis and fertilization are circumvented, the plants developing from such seed are genetically identical to the maternal plant. Expression of the leafy cotyledon 1 nucleic acid in the nucellus integument, or cell specific expression in the megaspore mother cell would trigger embryo formation from maternal tissues.

Producing a seed identical to the parent has many advantages. For example high yielding hybrids could be used in seed production to multiply identical copies of high yielding hybrid seed. This would greatly reduce seed cost as well as increase the number of genotypes which are commercially available. Genes can be evaluated directly in commercial hybrids since the progeny would not segregate. This would save years of back crossing. Apomixis would also provide a method of containment of transgenes when coupled with male sterility. The construction of male sterile autonomous agamospermy would prevent genetically engineered traits from hybridizing with weedy relatives.

Also gene stacking would be relatively easy with apomixis. Hybrids could be successively re-transformed with various new traits and propagated via apomixis. The traits would not need to be linked since apomixis avoids the problems associated with segregation. Apomixis can also provide a reduction in gene silencing. Gene silencing is frequently seen following meiotic divisions. Since meiotic divisions never occur, it may be possible to eliminate or reduce the frequency of gene silencing. Apomixis can also be used stabilize desirable phenotypes with complex traits such as hybrid vigor. Such traits could easily be maintained and multiplied indefinitely via apomixis.

Traditionally methods for genetic engineering in monocots, such as rice or maize, require a specific cell type as the recipient of new DNA. These cells are found in rapidly growing suspension and callus cells, or on the scutellar surface of the immature embryo (which gives rise to callus). Expression of the LEC1 nucleic acid can be used to stimulate embryo formation in tissues/genotypes normally not amenable to culture. Likewise ectopic expression in genotypes amenable to culture can increase the number of embryo precursor cells (or increase the number that develop into embryos) leading to an increase in transformation frequency, increase the growth rate and embryogenic character of transgenic calli, reduce the time needed to recover regenerable calli, and make regeneration of vigorous fertile plants easier and more reproducible. Transient expression using RNA or protein may be sufficient to initiate the cascade of events leading to embryo formation. This would be valuable in such target tissues as maize scutella, immature leaf bases, etc.

The LEC1 polynucleotide can also be used as a positive selectable marker, i.e. triggering embryogenesis in transgenic cells without killing the surrounding wild-type cells. The cells receiving the LEC1 polynucleotide would undergo embryogenesis or in tissues already undergoing embryogenesis LEC1 expression would stimulate more rapid reiteration and growth of somatic embryos. Thus transformed cells can be selected by their more rapid development of embryos.

It has been shown through sequence similarity that the Arabidopsis LEC1 polypeptide is homologous to the HAP3 subunit of the "CCAAT-box binding factor" class of eukaryotic transcriptional activators (Lotan et al., 1998, Cell 93:1195-1205). This class of proteins, which consist of Hap2/3 and 5, form a heterotrimeric transcriptional complex that appears to activate specific gene sets in eukaryotes. Certain members of this family such as Hap2 and Hap5 appear to be ubiquitously expressed, while different Hap3 members are under developmental or environmental regulation. Plant HAP3 polypeptides can be recognized by a high degree of sequence identity to other HAP3 homologs in the "B domain" of the protein. For example, the B domain for the Arabidopsis LEC1, from amino acid residue 28 to residue 117, shares between 55% and 63% identity (75-85% similarity) to other members of the HAP3 family, including maize (HAP3), chicken, lamprey, *Xenopus,* human, mouse, *Emericella nidulens, Schizosaccharomyces pombe, Saccharomyces cerevisiae* and *Kluuyveromyces lactis* (Lotan et al., 1998).

Expression of the LEC1 nucleic acid in transformed cells initiates embryo development and stimulates development of pre-existing embryos. Normally, LEC1 expression is necessary for proper embryo maturation in the latter stages of embryo development, and LEC1 transgene expression thus may also promote these processes. The combined effect of these impacts on somatic embryogenesis is not only to stimulate growth of transformed cells, but also to insure that transformed somatic embryos develop in a normal, viable fashion (increasing the capacity of transformed somatic embryos to germinate vigorously). Continued ectopic overexpression beyond embryo maturation may negatively impact germination and vegetative plant growth (which may necessitate down-regulation of the LEC1 transgene during these stages of development.

Expression of the LEC1 nucleic acid will stimulate growth in cells with the potential to initiate or maintain embryogenic growth. In addition, transformation methods that target certain reproductive tissues (or cells) such as vacuum-infiltration of *Agrobacterium* into *Arabidopsis* may have detrimental effects on recovery of transformants (triggering genes associated with embryogenesis may disrupt the proper functioning of these cells). Expression of LEC1 polynucleotides in transformants can help improve transformant recovery.

The polypeptides encoded by the present plant LEC1 genes can be distinguished from non-LEC HAP3 proteins by using the diagnostic motif shown in SEQ ID NO: 3.

The present invention further provides novel methods for transformation and for increasing transformation frequencies. A target plant cell is stably transformed with at least one growth stimulation vector to produce a modified target cell. The modified target cell is grown under conditions to produce at least one cell division to produce a progeny cell expressing the growth stimulation vector and then the progeny cell is transformed with one or more vectors containing a polynucleotide of interest operably linked to a promoter.

In another aspect of the invention a method for increasing transformation efficiency is provided comprising transforming a target plant cell with one or more vectors containing at least one polynucleotide of interest operably linked to a promoter, wherein the target cell has been previously modified to stimulate growth of the cell and the modified cell has gone through at least one cell division.

The modified cells can be obtained from T0 transgenic cultures, regenerated plants or progeny whether grown in vivo or in vitro so long as they exhibit stimulated growth compared to a corresponding cell that does not contain the modification. This includes but is not limited to transformed callus, tissue culture, regenerated T0 plants or plant parts such as immature embryos or any subsequent progeny of T0 regenerated plants or plant parts.

Once the target cell is transformed with the Lec1 nucleic acid, it is re-transformed with one or more genes of interest. The transformed cell can be from transformed callus, transformed embryo, T0 regenerated plants or its parts, progeny of T0 plants or parts thereof as long as the growth stimulation polynucleotide is present.

Polynucleotides of interest can include any polynucleotide, generally, those involved in oil, starch, protein, carbohydrate or nutrient metabolism as well as those affecting kernel size, sucrose loading, and the like. The polynucleotide of interest may be involved in regulating the influx of nutrients, disease resistance and in regulating expression of phytate genes particularly to lower phytate levels in the seed.

General categories of polynucleotides of interest for the purpose of present invention include for example, those genes involved in information, such as Zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, and grain characteristics. It is recognized that any polynucleotide of interest can be operably linked to the promoter of the invention and expressed in the seed.

Important traits such as oil, starch and protein content can be genetically altered. Modifications include altering the content of oleic acid, saturated and unsaturated oils, increasing levels of lysine and sulfur-containing amino acids and providing other essential amino acids, and also modification of starch and cellulose. Hordothionin protein modifications are described in WO94/16078; WO96/38562; WO96/08220; and U.S. Pat. No. 5,703,409 issued Dec. 30, 1997 the disclosures of which are incorporated herein in their entirety by reference. Another example is lysine and/or sulfur rich seed protein encoded by the soybean 2S albumin described in WO97/35023, and the chymotrypsin inhibitor from barley, Williamson et al. (1987) Eur. J. Biochem. 165:99-106, the disclosures of each are incorporated by reference.

Derivatives of the following genes can be made by site directed mutagenesis to increase the level of preselected amino acids in the encoded polypeptide. For example, the polynucleotide encoding the barley high lysine polypeptide (BHL) is derived from barley chymotrypsin inhibitor, WO98/20133, incorporated herein by reference. Other proteins include methionine-rich plant proteins such as from sunflower seed (Lilley et al. (1989) Proceedings of the World Congress on Vegetable Protein Utilization in Human Foods and Animal Feedstuffs; Applewhite, H. (ed.); American Oil Chemists Soc., Champaign, Ill.: pp. 497-502, incorporated herein in its entirety by reference), corn (Pedersen et al. (1986) J. Biol. Chem. 261:6279; Kirihara et al. (1988) Gene 71:359, both incorporated herein in its entirety by reference) and rice (Musumura et al. (1989) Plant Mol. Biol. 12:123, incorporated herein in its entirety by reference). Other agronomically important genes encode Floury 2, growth factors, seed storage factors and transcription factors.

Commercial traits can also be encoded on a gene(s) which could alter or increase for example, starch for the production of paper, textiles, and ethanol, or provide expression of proteins with other commercial uses. Another important commercial use of transformed plants is the production of polymers and bioplastics such as described in U.S. Pat. No. 5,602,321 issued Feb. 11, 1997. Genes such as B-ketothiolase, PHBase (polyhydroxyburyrate synthase) and acetoacetyl-CoA reductase (see Schubert et al. (1988) J. Bacteriol 170(12):5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of seed proteins, particularly modified seed proteins having improved amino acid distribution to improve the nutrient value of the seed, can be increased. This is achieved by the expression of such proteins having enhanced amino acid content.

Insect resistance genes may encode resistance to pests that have great yield drag such as rootworm, cutworm, European Corn Borer, and the like. Such genes include, for example, *Bacillus thuringiensis* endotoxin genes (U.S. Pat. Nos. 5,366,892; 5,747,450; 5,737,514; 5,723,756; 5,593,881; Geiser et al. (1986) Gene 48:109); lectins (Van Damme et al. (1994) Plant Mol. Biol. 24:825); and the like.

Genes encoding disease resistance traits may include detoxification genes, such as against fumonosin (U.S. patent application Ser. No. 08/484,815 filed Jun. 7, 1995); avirulence (avr) and disease resistance (R) genes (Jones et al. (1994) Science 266:789; Martin et al. (1993) Science 262: 1432; Mindrinos et al. (1994) Cell 78:1089; and the like.

Agronomic traits in seeds can be improved by altering expression of genes that affect the response of seed growth and development during environmental stress, Cheikh-N et al. (1994) Plant Physiol. 106(1):45-51) and genes controlling carbohydrate metabolism to reduce kernel abortion in maize, Zinselmeier et al. (1995) Plant Physiol. 107(2):385-391.

The polynucleotide of interest may be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired response. Thus the promoter sequences disclosed herein may be operably linked to antisense DNA sequences to reduce or inhibit expression of a native protein in the plant seed.

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In certain embodiments the monocot is corn, sorghum, barley, wheat, millet, or rice. Examples of suitable dicots include soybeans, sunflower, canola, alfalfa, potato, or cassaya.

Functional fragments included in the invention can be obtained using primers which selectively hybridize under stringent conditions. Primers are generally at least 12 bases in length and can be as high as 200 bases, but will generally be from 15 to 75, or from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3-8.5.9. Also, see generally, McPherson (ed.), *DIRECTED MUTAGENESIS: A Practical Approach,* (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alters, adds or deletes a single amino acid or a small percentage of amino acids in the encoded sequence is a "conservatively modified variant" where the alteration results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J. H., et al., *Proc. Natl. Acad. Sci. USA* 94:4504-4509 (1997).

The present invention also includes the use of 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387-395 (1984)) or MacVector 4.1 (Eastman Kodak Co., New Haven, Conn.).

For example, the inventive nucleic acids can be optimized for enhanced expression in plants of interest. See, for example, EPA0359472; WO 91/16432; Perlak et al. (1991) *Proc. Natl. Acad. Sci. USA* 88:3324-3328; and Murray et al. (1989) *Nucleic Acids Res.* 17:477-498. In this manner, the polynucleotides can be synthesized utilizing plant-preferred codons. See, for example, Murray et al. (1989) *Nucleic Acids Res.* 17:477-498, the disclosure of which is incorporated herein by reference.

The present invention provides subsequences comprising isolated nucleic acids containing at least 20 contiguous bases of the inventive sequences. For example the isolated nucleic acid includes those comprising at least 20, 25, 30, 40, 50, 60, 75, 100, 150, 200, 250, 300, 350, 400, and 500 contiguous nucleotides of the inventive sequences. Subsequences of the isolated nucleic acid can be used to modulate or detect gene expression. The subsequences can be used to decrease gene expression by with antisense and By "fragment" is intended a portion of the nucleotide sequence or a portion of the amino acid sequence and hence protein encoded thereby. Fragments of a nucleotide sequence may encode protein fragments that retain the biological activity of the native nucleic acid. Alternatively, fragments of a nucleotide sequence that are useful as hybridization probes may not encode fragment proteins retaining biological activity. Thus, fragments of a nucleotide sequence are generally greater than 25, 50, 100, 200, 300, 400, 500, 600, or 700 nucleotides and up to and including the entire nucleotide sequence encoding the proteins of the invention. Generally the probes are less than 1000 nucleotides and often less than 500 nucleotides. Fragments of the invention include antisense sequences used to decrease expression of the inventive polynucleotides. The fragments described above are useful in decreasing expression using antisense, hairpin, or cosuppression methods. Expression can be modulated by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics*, 37:327-336 (1996). Other methods for producing full-length libraries are known in the art. See, e.g., Edery et al., *Mol. Cell Biol.* 15(6):3363-3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, *Nuc. Acids. Res.* 18(19):5705-5711 (1990); Patanjali et al., *Proc. Natl. Acad. U.S.A.* 88:1943-1947 (1991); U.S. Pat. Nos. 5,482,685 and 5,637,685; and Soares et al., *Proc. Natl. Acad. Sci. USA* 91:9228-9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique* 3(2):58-63 (1991); Sive and St. John, *Nucl. Acids Res.* 16(22):10937 (1988); *Current Protocols in Molecular Biology*, Ausubel et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1-3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous polynucleotides in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

For purposes of defining the invention the following conditions are provided. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C. Typically the time of hybridization is from 4 to 16 hours.

An extensive guide to the hybridization of nucleic acids is found in Tijssen, *Laboratory Techniques in Biochemistry and Molecular Biology—Hybridization with Nucleic Acid Probes*, Part I, Chapter 2 "*Overview of principles of hybridization and the strategy of nucleic acid probe assays*", Elsevier, N.Y. (1993); and *Current Protocols in Molecular Biology*, Chapter 2, Ausubel, et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related polynucleotides directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products. PCR-based screening methods have also been described. Wilfinger et al. describe a PCR-based method in which the longest cDNA is identified in the first step so that incomplete clones can be eliminated from study. *BioTechniques*, 22(3): 481-486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues. Good results have been obtained using mitotically active tissues such as shoot meristems, shoot meristem cultures, embryos, callus and suspension cultures, immature ears and tassels, and young seedlings. The cDNAs of the present invention were obtained from immature zygotic embryo and regenerating callus libraries.

Alternatively, the sequences of the invention can be used to isolate corresponding sequences in other organisms, particularly other plants, more particularly, in dicots or other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90-99 (1979); the phosphodiester method of Brown et al., *Meth. Enzymol.* 68:109-151 (1979); the diethylphosphoramidite method of Beaucage et al., *Tetra. Lett* 22:1859-1862 (1981); the solid phase phosphoramidite triester method described by Beaucage and Caruthers, *Tetra. Letts.* 22(20):1859-1862 (1981), e.g., using an automated synthesizer, e.g., as described in Needham-VanDevanter et al., *Nucleic Acids Res.* 12:6159-6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A Laboratory Manual*; Cold Spring Harbor, N.Y.; (1989); Gelvin, et al.; *Plant Molecular Biology Manual* (1990); *Plant Biotechnology: Commercial Prospects and Problems*, eds. Prakash, et al.; Oxford & IBH Publishing Co.; New Delhi, India; (1993); and Heslot et al.; *Molecular Biology and Genetic Engineering of Yeasts*; CRC Press, Inc., USA; (1992); each incorporated herein in its entirety by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the actin promoter, the ubiquitin promoter, the histone H2B promoter (Nakayama et al., 1992, FEBS Lett 30:167-170), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known in the art.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47:95-102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18(21): 6426 (1990). See the following site relating to the waxy promoter: Kloesgen, R. B., Gierl, A., Schwarz-Sommer, Z. S. and Saedler, H., Molecular analysis of the waxy locus of *Zea mays, Mol. Gen. Genet.* 203:237-244 (1986). The disclosures each of these are incorporated herein by reference in their entirety.

A weak constitutive promoter, such as the Nos promoter, an inducible promoter, such as In2, or a nucellus-preferred or integument-preferred promoter can be used to induce apospory. For example the barley or maize Nuc1 promoter, the maize Cim 1 promoter or the maize LTP2 promoter can be used to preferentially express in the nucellus. See for example WO 00/11177 the disclosure of which is incorporated herein by reference.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395-4405 (1988); Callis et al., *Genes Dev.* 1:1183-1200 (1987). Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotics spectinomycin and streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

While useful in conjunction with the above antibiotic and herbicide-resistance selective markers (i.e. use of the LEC1 gene can increase transformation frequencies when using chemical selection), another use of LEC1 expression takes advantage of this gene conferring a growth advantage to transformed cells without the need for inhibitory compounds to retard non-transformed growth. Thus, LEC1 transformants are recovered based solely on their differential growth advantage.

Typical vectors useful for expression of genes in higher plants are well known in the art and include vectors derived from the tumor-inducing (Ti) plasmid of *Agrobacterium tumefaciens* described by Rogers et al., Meth. In Enzymol. 153:253-277 (1987). Exemplary *A. tumefaciens* vectors useful herein are plasmids pKYLX6 and pKYLX7 of Schardl et al., Gene, 61:1-11 (1987) and Berger et al., *Proc. Natl. Acad. Sci. USA* 86:8402-8406 (1989). Another useful vector herein is plasmid pBI101.2 that is available from Clontech Laboratories, Inc. (Palo Alto, Calif.). A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Natl. Acad. Sci. USA* 85:8805-8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279-289 (1990) and U.S. Pat. No. 5,034,323. Recent work has shown suppression with the use of double stranded RNA. Such work is described in Tabara et al., *Science* 282:5388:430-431 (1998). Hairpin approaches (also referred to as stem loop or inverted repeat sequences) of gene suppression are disclosed in WO 98/53083 and WO 99/53050.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585-591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065-4076, describe covalent bonding of a single-stranded DNA fragment with alkylating derivatives of nucleotides complementary to target sequences. A report of similar work by the same group is that by Knorre, D. G., et al., *Biochimie* (1985) 67:785-789. Iverson and Dervan also showed sequence-specific cleavage of single-stranded DNA mediated by incorporation of a modified nucleotide which was capable of activating cleavage (*J. Am. Chem. Soc.* (1987) 109:1241-1243). Meyer, R. B., et al., *J. Am. Chem. Soc.* (1989) 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197-3203. Use of crosslinking in triple-helix forming probes was also disclosed by Home et al., *J. Am. Chem. Soc.* (1990) 112:2435-2437. Use of N4,N4-ethanocytosine as an alkylating agent to crosslink to single-stranded oligonucleotides has also been described by Webb and Matteucci, *J. Am. Chem. Soc.* (1986) 108:2764-2765; *Nucleic Acids Res* (1986) 14:7661-7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

The isolated proteins of the present invention include a polypeptide comprising at least 20 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 30 to the number of residues in a full-length polypeptide of the present invention. Optionally, this subsequence of contiguous amino acids is at least 25, 30, 35, 40, 50, 60, 70, 80, 90, 100, 150, 200, 250, 300, 350, 400, 450, or 500 amino acids in length.

The present invention includes catalytically active polypeptides (i.e., enzymes). Catalytically active polypeptides will generally have a specific activity of at least 20%, 30%, or 40%, 50%, 60%, 70%, 80%, 90%, 95%, 100% or greater than that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, 50%, 60%, 70%, 80%, 90%, 100% or greater than that of the native (non-synthetic), endogenous polypeptide. Methods of assaying and quantifying measures of enzymatic activity and substrate specificity ($k_{cat}/K_m$), are well known to those of skill in the art.

The present invention includes modifications that can be made to an inventive protein. In particular, it may be desirable to diminish the activity of the LEC1 gene. Other modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in a recombinantly engineered cell such as bacteria, yeast, insect, mammalian, or plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the polynucleotide of interest can be isolated in significant quantities for introduction into the desired plant cells.

Host cells that can be used in the practice of this invention include prokaryotes, including bacterial hosts such as *Eschericia coli, Salmonella typhimurium*, and *Serratia marcescens*. Eukaryotic hosts such as yeast or filamentous fungi may also be used in this invention. Since these hosts are also microorganisms, it will be essential to ensure that plant promoters which do not cause expression of the polypeptide in bacteria are used in the vector.

Commonly used prokaryotic control sequences include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva et al., *Gene* 22:229-235 (1983); Mosbach et al., *Nature* 302:543-545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology. Vol. 2: Special Methods in Peptide Synthesis, Part A.;* Merrifield et al., *J. Am. Chem. Soc.* 85:2149-2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant.

The method comprises transforming a plant cell with an expression cassette comprising a polynucleotide of the present invention to obtain a transformed plant cell, growing the transformed plant cell under conditions allowing expression of the polynucleotide in the plant cell in an amount sufficient to modulate concentration and/or composition in the plant cell.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein. It has been observed that high levels of LEC1 prevent germination. See Lotan et al., Cell 1998 Jun. 26; 93(7):1195-1205. Thus, temporal regulation of LEC1 expression may be desirable in certain species to permit proper germination, vegetative growth, flowering and reproduction.

In some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, the level of protein is increased or decreased by at least 5%, 10%, 20%, 30%, 40%, 50%, 60%, 70%, 80%, 90%, 100% or greater relative to a corresponding control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In certain embodiments, the polypeptides of the present invention are modulated in monocots or dicots, examples include maize, soybeans, sunflower, sorghum, canola, wheat, alfalfa, rice, barley and millet.

Means of detecting the proteins of the present invention are not critical aspects of the present invention. The proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, 30%, 40%, 50%, 60%, 70%, 80%, 90% of the specific activity of the native, full-length polypeptide of the present invention (e.g., enzyme) or greater. Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations.

Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495-497 (1975).

Other suitable techniques involve selection of libraries of recombinant antibodies in phage or similar vectors (see, e.g., Huse et al., *Science* 246:1275-1281 (1989); and Ward et al., *Nature* 341:544-546 (1989); and Vaughan et al., *Nature Biotechnology*, 14:309-314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845-851 (1996). Also, recombinant immunoglobulins may be produced. See, Cabilly, U.S. Pat. No. 4,816,567; and Queen et al., *Proc. Natl. Acad. Sci.* 86:10029-10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A DNA sequence coding for the desired polynucleotide of the present invention, for example a cDNA or a genomic sequence encoding a full length protein, can be used to construct an expression cassette which can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421-477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197-213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3:2717-2722 (1984). Electroporation techniques are described in Fromm et al., *Proc. Natl. Acad. Sci.* 82:5824 (1985). Ballistic transformation techniques are described in Klein et al., *Nature* 327:70-73 (1987).

*Agrobacterium tumefaciens*-meditated transformation techniques are well described in the scientific literature. See, for example Horsch et al., *Science* 233:496-498 (1984), and Fraley et al., *Proc. Natl. Acad. Sci.* 80:4803 (1983). For instance, *Agrobacterium* transformation of maize is described in U.S. Pat. No. 5,981,840. *Agrobacterium* transformation of soybean is described in U.S. Pat. No. 5,563,055.

Other methods of transfection or transformation include (1) *Agrobacterium rhizogenes*-mediated transformation (see, e.g., Lichtenstein and Fuller In: Genetic Engineering, Vol. 6, PWJ Rigby, Ed., London, Academic Press, 1987; and Lichtenstein, C. P., and Draper, J., In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25:1353, (1984)), (3) the vortexing method (see, e.g., Kindle, *Proc. Natl. Acad. Sci. USA* 87:1228, (1990)).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding polynucleotides can be obtained by injection of the DNA into reproductive organs of a plant as described by Pena et al., Nature, 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27-54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

The present invention contemplates the use of various gene targeting methods. Insertion, excision or recombination sites for use in the invention are known in the art and include FRT or lox sites (see, for example, Schlake et al. (1994) *Biochemistry* 33:12746-12751; Huang et al. (1991) *Nucleic Acids Res.* 19:443-448; Sadowski (1995) *Prog. Nuc. Acid Res. Mol. Bio.* 51:53-91; Cox (1989) *Mobile DNA*, ed. Berg and Howe (American Society of Microbiology, Washington D.C.), pp. 116-670; Dixon et al. (1995) 18:449-458; Umlauf et al. (1988) *EMBO J.* 7:1845-1852; Buchholz et al. (1996) *Nucleic Acids Res.* 24:3118-3119; Kilby et al. (1993) *Trends Genet.* 9:413-421; Roseanne et al. (1995) *Nat Med.* 1:592-594; Albert et al. (1995) *Plant J.* 7:649-659; Bailey et al. (1992) *Plant Mol. Biol.* 18:353-361; Odell et al. (1990) *Mol. Gen. Genet* 223:369-378; and Dale et al. (1991) *Proc. Natl. Acad. Sci. USA* 88:10558-105620; lox (Albert et al. (1995) *Plant J.* 7:649-659; Qui et al. (1994) *Proc. Natl. Acad. Sci. USA* 91:1706-1710; Stuurman et al. (1996) *Plant Mol. Biol.* 32:901-913; Odell et al. (1990) *Mol. Gen. Genet* 223:369-378; Dale et al. (1990) *Gene,* 91:79-85; and Bayley et al. (1992) *Plant Mol. Biol.* 18:353-361); U.S. Pat. No. 5,658,772; U.S. Pat. No. 4,959,317; U.S. Pat. No. 6,110,736. Such recombination sites in the presence of a compatible recombinase allow for the targeted integration of one or more nucleotide sequences of interest into the plant genome. It is recognized that variations of targeted insertion can also be practiced with the invention. See for example WO 99/25821; WO 99/25855; WO 99/25840; WO 99/25853. The disclosures of the above are herein incorporated by reference.

It may be desirable to reduce the likelihood of ectopic stable expression of the LEC1 gene. Strategies for transient-only expression can be used. This includes delivery of RNA (transcribed from the LEC1 gene), chemically end-modified DNA expression cassettes that typically will not integrate, or LEC1 protein along with the transgene cassettes to be integrated to enhance transgene integration by transient stimulation of cell division. Using well-established methods to produce LEC1-RNA, this can then be purified and introduced into maize cells using physical methods such as microinjection, bombardment, electroporation or silica fiber methods.

For protein delivery, the gene is first expressed in a bacterial or baculoviral system, the protein purified and then introduced into maize cells using physical methods such as microinjection, bombardment, electroporation or silica fiber methods. Alternatively, LEC1 proteins can be delivered from *Agrobacterium tumefaciens* into plant cells in the form of fusions to *Agrobacterium* virulence proteins. Fusions can be constructed between LEC1 and bacterial virulence proteins such as VirE2, VirD2, or VirF, which are delivered directly into plant cells. Fusions are constructed to retain both those properties of bacterial virulence proteins required to mediate delivery into plant cells and the LEC1 activity required for enhancing transgene integration. This method ensures a high frequency of simultaneous co-delivery of T-DNA and functional LEC1 protein into the same host cell. The methods above represent various means of using the LEC1 nucleic acid or its encoded product to transiently stimulate DNA replication and cell division, which in turn enhances transgene integration by providing an improved cellular/molecular environment for this event to occur. The method is described in WO 99/61619 which is incorporated herein by reference.

Altering the Culture Medium to Suppress Somatic Embryogenesis in Non-Transformed Plant Cells and/or Tissues to Provide for a Positive Section Means of Transformed Plant Cells Using the following methods for controlling somatic embryogenesis, it is possible to alter plant tissue culture media components to suppress somatic embryogenesis in a plant species of interest (often having multiple components that potentially could be adjusted to impart this effect). Such conditions would not impart a negative or toxic in vitro environment for wild-type tissue, but instead would simply not produce a somatic embryogenic growth form. Introducing a transgene such as LEC1 will stimulate somatic embryogenesis and growth in the transformed cells or tissue, providing a clear differential growth screen useful for identifying transformants.

Altering a wide variety of media components can modulate somatic embryogenesis (either stimulating or suppressing embryogenesis depending on the species and particular media component). Examples of media components which, when altered, can stimulate or suppress somatic embryogenesis include;
1) the basal medium itself (macronutrient, micronutrients and vitamins; see T. A. Thorpe, 1981 for review, "Plant Tissue Culture: Methods and Applications in Agriculture", Academic Press, NY),
2) plant phytohormones such as auxins (indole acetic acid, indole butyric acid, 2,4-dichlorophenoxyacetic acid, naphthaleneacetic acid, picloram, dicamba and other functional analogues), cytokinins (zeatin, kinetin, benzyl amino purine, 2-isopentyl adenine and functionally-related compounds) abscisic acid, adenine, and gibberellic acid,
3) and other compounds that exert "growth regulator" effects such as coconut water, casein hydrolysate, and proline, and
4) the type and concentration of gelling agent, pH and sucrose concentration.

Changes in the individual components listed above (or in some cases combinations of components) have been demonstrated in the literature to modulate in vitro somatic embryogenesis across a wide range of dicotyledonous and monocotyledonous species. For a compilation of examples, see E. F. George et al. 1987. Plant Tissue Culture Media. Vol. 1: Formulations and Uses. Exergetics, Ltd., Publ., Edington, England.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., *The Plant Cell,* 2:603-618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell*

*Culture*, Macmillan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* can be achieved as described by Horsch et al., *Science*, 227:1229-1231 (1985) and Fraley et al., *Proc. Natl. Acad. Sci. U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467-486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings, via production of apomictic seed, or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

In one embodiment a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated. Alternatively, propagation of heterozygous transgenic plants could be accomplished through apomixis.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants which can be used in the method of the invention include monocotyledonous and dicotyledonous plants. Particular plants include maize, wheat, rice, barley, oats, sorghum, millet, rye, soybean, sunflower, alfalfa, canola and cotton.

Seeds derived from plants regenerated from transformed plant cells, plant parts or plant tissues, or progeny derived from the regenerated transformed plants, may be used directly as feed or food, or further processing may occur.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

EXAMPLES

Example 1

Identification and Cloning of the Rice LEC1 Gene

Using the ZmLEC1 sequence as a blast query a rice LEC1 sequence was identified in Contig 31520 in the Rice Genomic DNA database (BG1, China). See Yu et al. (2002) Science 296:79-92. At the DNA level the rice and maize sequences are 79% identical. The genomic Rice sequence was amplified from rice genomic DNA using the following primers; 5'ATGCCTCTCTACGGCTAGCTACTCC3' SEQ ID NO:4 and 5'CGCCATTCTGCTGCTGTTAC3' SEQ ID NO:5. PCR was set up using Qiagen's Hot Star TAQ with Q solution according to the manufactures instructions. PCR was run as follows:

| | |
|---|---|
| Step 1 | 15 minutes at 95° C. |
| Step 2 | 0.5 minutes at 94° C. |
| Step 3 | 0.75 minutes at 60° C. |
| Step 4 | 1 minute at 72° C. |
| Step 5 | go to step 2, 30 times |
| Step 6 | 10 minutes at 72° C. |
| Step 7 | Hold at 4° C. |

The resulting 965 bp product was then cloned into a TOPO TA cloning vector (Invitrogen), sequenced and cloned into an expression cassette driven by the *Agrobacterium* nopaline synthase promoter (nos) with a potato proteinase inhibitor 3'polyadenylation sequence (pinII). The rice LEC1 sequence differed from the sequence in Contig 31520 by only one base.

Example 2

Transformation and Regeneration of Maize Callus

Immature maize embryos from greenhouse or field grown High type II donor plants were bombarded with a plasmid containing the rice LEC1 polynucleotide (OsLEC1). The LEC1 polynucleotide was operably linked to a constitutive promoter such as nos, or an inducible promoter, such as In2, and a 3' regulatory sequence such as the potato proteinase inhibitor 3' sequence, pinII. The plasmid containing nos:: OsLEC1::pinII was introduced with a second plasmid containing the selectable marker gene PAT (Wohileben et al. (1988) *Gene* 70:25-37) that confers resistance to the herbicide Bialaphos fused to the Green Fluorescence protein. Transformation was performed as follows.

The ears were surface sterilized in 50% Chlorox bleach plus 0.5% Micro detergent for 20 minutes, and rinsed two times with sterile water. The immature embryos were excised and placed embryo axis side down (scutellum side up), 25 embryos per plate. These were cultured on 560 L medium 4 days prior to bombardment in the dark. Medium 560 L is an N6-based medium containing Eriksson's vitamins, thiamine, sucrose, 2,4-D, and silver nitrate. The day of bombardment, the embryos were transferred to 560 Y medium for 4 hours and were arranged within the 2.5-cm target zone. Medium 560Y is a high osmoticum medium (560L with high sucrose concentration).

The nos::OsLEC1::pinII DNA plus plasmid DNA containing the PAT selectable marker (UBI::PAT~GFP::pinII) was precipitated onto 0.6 μm (average diameter) gold pellets using a $CaCl_2$ precipitation procedure as follows: 100 μl prepared gold particles (0.6 mg) in water, 20 μl (2 μg) DNA in TrisEDTA buffer (1 μg total), 100 μl 2.5 M $CaCl_2$, 40 μl 0.1 M spermidine.

Each reagent was added sequentially to the tungsten particle suspension. The final mixture was sonicated briefly. After the precipitation period, the tubes were centrifuged briefly, liquid removed, washed with 500 ml 100% ethanol, and centrifuged again for 30 seconds. Again the liquid was removed, and 60 μl 100% ethanol was added to the final tungsten particle pellet. For particle gun bombardment, the tungsten/DNA particles were briefly sonicated and 5 μl spotted onto the center of each macrocarrier and allowed to dry about 2 minutes before bombardment.

The sample plates were bombarded at a distance of 8 cm from the stopping screen to the tissue, using a DuPont biolistics helium particle gun. All samples received a single shot at 650 PSI, with a total of ten aliquots taken from each tube of prepared particles/DNA.

Four to 12 hours post bombardment, the embryos were moved to 560P (a low osmoticum callus initiation medium similar to 560L but with lower silver nitrate), for 3-7 days, then transferred to 560R selection medium, an N6 based medium similar to 560P containing 3 mg/liter Bialaphos, and subcultured every 2 weeks. Multicellular GFP cell clusters became visible after two weeks and their numbers were periodically recorded. After approximately 10 weeks of selection, selection-resistant GFP positive callus clones were sampled for PCR and activity of the polynucleotide of interest. Positive lines were transferred to 288J medium, an MS-based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the polynucleotide of interest.

Example 3

Ectopic Expression of OsLEC1 to Induce Somatic Embryogenesis

Using the genotype High type II as an example, embryos were isolated and cultured on 560L medium for 3-5 days. Four to twelve hours before bombardment these embryos were transferred to high osmotic 560Y medium. Expression cassettes containing the OsLEC1 cDNA were then co-introduced into the scutella of these embryos along with an expression cassette containing the Pat gene fused to the Green Fluorescent protein using methods described in Example 2. Embryos from a single ear were divided evenly between treatments. Four to 12 hours following bombardment embryos were then transferred back to a low osmoticum callus initiation medium (560P) and incubated in the dark at 26° C. After 3-7 days of culture these embryos were moved to 560R selection medium. Cultures were then transferred every two weeks until transformed colonies appear. Cultures were also examined microscopically for GFP expression. OsLEC1 expression was expected to stimulate adventive embryo formation. This was apparent when the cultures were compared to controls (transformed without the OsLEC1 cDNA or non-induced).

A. Transformation Frequency was Improved by OsLEC1 Introduced Using Particle-Mediated DNA Delivery Expression cassettes were made to evaluate the effects of OsLEC1 on maize transformation. The rice LEC1 polynucleotide (OsLEC1) was placed under the control of the nos promoter (weakly expressed constitutively). A version without a promoter in front of the LEC1 nucleic acid was made for use as a negative control. A plasmid containing nos::ZmLEC1::pinII (maize LEC1 with the same 5' and 3' regulatory elements used for the rice nucleic acid) served as a positive control. Each of these constructs were co-bombarded with the Pat~GFP fusion construct (designated as PAT~GFP) into high type II embryos as described in Example 2. Also, as in Example 2, immature embryos were harvested from separate ears, and the embryos from each ear were divided equally between treatments to account for ear-to-ear variability. Transformation frequency was determined by counting the number of embryos with large multicellular GFP-positive cells clusters using a GFP microscope, and representing these as a percentage of the original number of embryos bombarded for that treatment. No distinction was made between embryos with single or multiple events. The functional OsLEC1 expression cassette significantly increased transformation over the control treatment, producing transgenic events at 20.0% (+/−4.9) and 5.6% (+/−4.7) frequencies, respectively. The maize LEC1 expression cassette also significantly increased transformation (20.8%+/−7.7) relative to the control. The maize and rice LEC1 genes produced results that were similar (Student's T-test; p=0.05 for all statistical comparisons). The OsLEC1 expression cassette also increased the incidence of multiple, i.e. 2-3, multicellular transgenic clones growing from the same immature embryo, but as stated above we only scored these as a single event, and are providing a conservative representation of OsLEC1's ability to improve transformation. In addition to increasing the absolute number of transformants recovered from a given amount of target tissue, OsLEC1 transformants appeared earlier than the control transformants (suggesting that the OsLEC1 polynucleotide also stimulated growth rates).

Increasing the promoter strength (driving OsLEC1 expression) increases transformation frequencies. For example, an experiment is performed to compare the In2, nos and UBI promoters. Based on our experience with these promoters driving other genes, the In2 promoter (in the absence of an inducer other than auxin from the medium) drives expression at very low levels. The nos promoter drives moderately-low levels of transgene expression (approximately 10- to 20-fold lower than the maize ubiquitin promoter, but still stronger than In2 under the culture conditions used in this experiment). As a control treatment, the frame-shifted OsLEC1 driven by the In2 promoter is used. The control treatment results in low transformation frequencies, while for the In2:OsLEC1, nos:OsLEC1 and UBI:OsLEC1 treatments progressively higher transformation frequencies are observed.

B. Transformation Frequency is Improved by LEC1 Introduced Using *Agrobacterium*

Vectors containing either Ubi::moPAT~GFPm::pinII alone (control treatment) or Ubi::moPAT~GFPm::pinII+ nos::OsLEC1::pinII (OsLEC1 treatment) are mated into *Agrobacterium tumefaciens* LBA4404 carrying a superbinary vir plasmid. The *Agrobacterium* strains containing the superbinary plasmids and *Agrobacterium*-mediated DNA delivery method are described by U.S. Pat. No. 5,981,840. Briefly, colonies containing the engineered *Agrobacterium* are grown to log phase in minimal A medium. Log phase cells are collected by centrifugation and resuspended in 561Q medium (N6 salts, Eriksson's vitamins, 1.5 mg/l 2,4-D, 68.5 g/l sucrose, 36 g/l glucose, plus 20 mg/l acetosyringone). Immature embryos, 1.5-2 mm in length, are excised and immersed in this solution at a concentration of $5 \times 10^8$ bacterial cells/ml. Embryos are vortexed in this medium and allowed to sit for 5 minutes. The embryos are then removed and placed on 562P medium (560P medium with 100 mM acetosyringone and incubated at 20° C. for 3 days. Embryos are moved again to 563N medium (an agar solidified medium similar to 560P with 100 mg/l carbenicillin, 0.5 g/l MES and reduced 2,4-D) and cultured at 28° C. for 3 days. Embryos are then moved to 563O medium (563N medium with 3 mg/l bialaphos) and transferred thereafter every 14 days to fresh 563O medium.

Bialaphos resistant GFP+ colonies are counted using a GFP microscope and transformation frequencies are determined as described in Example 3. Similar to particle gun experiments, transformation frequencies are expected to be increased in the OsLEC1 treatment.

C. Transformants are Recovered Using LEC1 Expression Under Reduced Auxin Levels or in the Absence of Auxins in the Medium, and in the Absence of Herbicide or Antibiotic Selection.

To determine if OsLEC1 could be used in a positive selection scheme, particle gun transformation experiments are initiated as described in Example 2 and transformants are selected on medium with normal auxin levels, or on medium with reduced or no auxin, or visually (using GFP) on medium without bialaphos. Transformation frequencies are based on the numbers of embryos with one or more multicellular GFP positive cell clusters. In the first experiment to test this concept, there are two treatment variables. The first is that immature embryos are bombarded with the control plasmid (UBI:PAT~GFP) or with UBI:PAT~GFP+nos::OsLEC1. The second variable is that the bombarded embryos are divided onto either normal bialaphos-containing selection medium (with normal auxin levels of 2 mg/l 2,4-D), or medium with no bialaphos and reduced 2,4-D levels (0.5 mg/l). On bialaphos selection the OsLEC1 treatment is expected to result in a higher transformation frequency than the control. It is also expected that the low auxin medium (0.5 mg/l 2,4-D) will result in reduced growth rates. Consistent with this, for the control plasmid treatment (UBI:PAT~GFP), recovery of GFP-expressing (fluorescent) colonies should be reduced relative to highly-effective bialaphos-selection treatment. In contrast, OsLEC1 expression, through its stimulation of embryogenesis, should compensate for the low auxin environment, providing a growth advantage to the transgenic colonies, and maintaining the efficiency of transformant recovery at high levels (still in the same range as the OsLEC1/bialaphos-selected treatment). The inclusion of OsLEC1 is expected to improve colony growth on reduced auxin relative to the control.

On medium completely devoid of auxin, colonies are only observed in the OsLEC1 treatment. In this experiment, immature embryos are bombarded with either the control plasmid (UBI:PAT~GFP) or with UBI:PAT~GFP+nos::OsLEC1, and then plated either onto 3.0 mg/l bialaphos, 2.0 mg/l 2,4-D medium or onto no-bialaphos, no 2,4-D medium (in this latter treatment, wild-type maize callus will not exhibit embryogenic growth). The OsLEC1 polynucleotide is expected to increase transformation relative to the control plasmid on normal auxin-containing, bialaphos selection medium. Also, it is expected, that no transformants are recovered with the control plasmid on medium devoid of exogenous auxin. In the OsLEC1 treated embryos, transformants are expected to be recovered at a frequency higher than the control plasmid on bialaphos selection.

Even on auxin-containing medium, the OsLEC1 polynucleotide in combination with GFP+ expression can be used to recover transformants without chemical selection. For example, under these conditions the recovery of transformants is relatively efficient as compared to bialaphos selection, but this requires more diligence than the low- or no-auxin treatments above to separate the GFP-expressing colonies from the growing callus population.

D. OsLEC1 Improves the Embryogenic Phenotype and Regeneration Capacity of Inbreds.

Immature embryos from the inbred PHP38 are isolated, cultured and transformed as described in example 2 with the following changes. Embryos are initially cultured on 601H medium (a MS based medium with 0.1 mg/l zeatin, 2 mg/l 2,4-D, MS and SH vitamins, proline, silver nitrate, extra potassium nitrate, casein hydrolysate, gelrite, 10 g/l glucose and 20 g/l sucrose). Prior to bombardment embryos are moved to a high osmoticum medium (modified Duncan's with 2 mg/l 2,4-D and 12% sucrose). Post bombardment, embryos are moved to 601H medium with 3 mg/l bialaphos for two weeks. Embryos are then moved to 601H medium without proline and casein hydrolysate with 3 mg/l bialaphos and transferred every two weeks. Transformation frequency is determined by counting the numbers of bialaphos resistant GFP-positive colonies. Colonies are also scored on whether they had an embryogenic (regenerable) or non-embryogenic phenotype. In PHP38, the OsLEC1 polynucleotide increases transformation frequency and improves the regenerative potential of the callus. For example, a balanced experiment (the embryos from each harvested ear are divided equally between treatments) is conducted in which PHP38 immature embryos are bombarded with the control plasmid (UBI::PAT~GFP::pinII) in one treatment, with the UBI::PAT~GFP::pinII plasmid+In2::OsLEC1, or with the UBI::PAT~GFP::pinII plasmid+nuc1::OsLEC1 (a maize nucellus-specific promoter driving OsLEC1 expression). The frequency of GFP+ calli growing on bialaphos-containing media (relative to the starting number of embryos) is determined 6 weeks after bombardment. For the control treatment, the transformation frequency is low, while for the In2:OsLEC1 and nuc1::OsLEC1 treatments the transformation frequencies are higher. In addition, the presence of the OsLEC1 polynucleotide should improve the regeneration capacity of the recovered transformants. Few of the control transformants (UBI::PAT~GFP::pinII alone) has an embryogenic, regenerable phenotype, while the transformants from the In2:OsLEC1 and nuc1::OsLEC1 treatments should exhibit a more vigorous, embryogenic growth pattern. This is born out in the ability to recover plants. Callus from the In2:OsLEC1 and nuc1::OsLEC1 treatments should produce many healthy plants.

Example 4

Use of the Rice LEC1 to Induce Apomixis

Maize expression cassettes directing OsLEC1 expression to the inner integument or nucellus can easily be constructed. An expression cassette directing expression of the OsLEC1 polynucleotide to the nucellus is made using the barley Nuc1 promoter. Embryos are co-bombarded with the selectable marker PAT fused to the GFP gene along with the nucellus specific OsLEC1 expression cassette described above. Both inbred (PHP38) and GS3 transformants are obtained and regenerated as described in examples 2 and 3. Transformation frequencies should be increased over the control using the nuc1:LEC1 polynucleotide (see Example 3 above).

It is anticipated that the regenerated plants will then be capable of producing de novo embryos from OsLEC1 expressing nucellar cells. This is complemented by pollinating the ears to promote normal central cell fertilization and endosperm development. In another variation of this scheme, nuc1:OsLEC1 transformations could be done using a FIE-null genetic background which would promote both de novo embryo development and endosperm development without fertilization (see Ohad et al. 1999 The Plant Cell 11:407-415; also WO 01/16325). Upon microscopic examination of the developing embryos it will be apparent that apomixis has occurred by the presence of embryos budding off the nucellus. In yet another variation of this scheme the OsLEC1 polynucleotide could be delivered as described above into a homozygous zygotic-embryo-lethal genotype. Only the adventive embryos produced from somatic nucellus tissue would develop in the seed.

Example 5

OsLEC1 Expression Results in Increased Growth Rates, which can be Used as a Screening Criterion for Positive Selection of Transformants Using two promoters of increasing strength to drive OsLEC1 expression in maize, it is expected that OsLEC1 stimulates callus growth over control treatments and the stronger promoter driving OsLEC1 results in faster growth than with the low-level promoter. For example, an experiment to compare the In2 and nos promoters can be conducted. As noted above, based on our experience with these two promoters driving other genes, the In2 promoter (in the absence of an inducer other than auxin from the medium) would drive expression at very low levels. The nos promoter has been shown to drive moderately-low levels of transgene expression (approximately 10- to 30-fold lower than the maize ubiquitin promoter, but still stronger than In2 under the culture conditions used in this experiment). One control treatment is used in this experiment, the UBI:PAT~GFPmo:pinII construct by itself (with no OsLEC1). Hi-II immature embryos are bombarded as previously described, and transgenic, growing events are scored at 3 and 6 weeks. The control treatment is expected to result in a low transformation frequency. The In2:LEC1 and nos:LEC1 treatments are expected to result in moderate transformation frequencies that are higher than the control treatment.

Within these treatments there is also expected an increase in the overall frequency of large, rapidly growing calli, relative to the control treatment. For this data, the fresh weight of transformed calli are recorded 2 months after bombardment. Assuming that all the transgenic events started as single transformed cells within a few days after bombardment, these weights represent the relative growth rate of these transformants during this period (all tissue is sub-cultured and weighed for each transformant; mean weights and standard deviations are calculated for each treatment). Relative to the mean transformant weight for the control treatment, it is expected that the In2:LEC1 and nos:LEC1 treatments produce mean transformant weights that are 3-fold and 10-fold higher, respectively. It is expected that increasing LEC1 expression results in a concomitant increase in callus growth rate.

Example 6

Re-Transformation of OsLEC1 Transgenic Progeny Results in Increased Transformation Frequency in Elite Maize Inbreds Two vectors are used to create stable transgenic inbred events to test re-transformation. A control vector carries two gene cassettes. The first comprises a ubiquitin promoter: intron sequence driving a Green Fluorescent Protein (GFP) coding sequence. This coding sequence is codon optimized for expression in maize and to include an intron (precluding expression of the GFP in bacterial cells). A polyadenylation signal sequence from the pinII gene is used. The second gene in this vector is the selectable marker CaMV35S Enhancer:CaMV35S promoter:Omega Prime 5'UTR:ADH1 intron1:BAR:pinII. This control vector is mated into *Agrobacterium tumefaciens* LBA4404 carrying a superbinary vir plasmid (PHP10523). The second vector contains the nos::OsLEC1::pinII expression cassette+UBI::GFPm::pinII/35S::bar::pinII.

The visible marker gene GFP (green fluorescence protein; Chalfie et al., Science 263:802, 1994) has been described as has the maize-optimized GFP (GFPm; see copending US Patent Application WO 97/41228). The Ubiquitin promoter has been described (Christensen et al., Plant Mol. Biol. 12: 619-623 (1989) and Christensen et al., Plant Mol. Biol. 18: 675-689 (1992), as has the pinII (An et al., 1989, Plant Cell 1: 115-122) 3' region used in these cassettes.

Transformations of the OsLEC1-containing plasmid and control plasmid in the maize inbred P38 are done using the *Agrobacterium* mediated DNA delivery method. Embryos are co-cultured on culture medium with acetosyringone for 7 days at 20° C. After 7 days the embryos are transferred to standard culture medium containing 3 mg/L Bialaphos with the addition of 100 mg/L carbenicillin to kill off residual Agrobacteria. Total embryos cultured per ear are divided between the two plasmids to evaluate the effect of OsLEC1 on inbred transformation. Fertile plants with normal phenotypes are recovered based on reporter gene expression, leaf resistance to herbicide, and molecular analyses in both OsLEC1 events and in control events containing only BAR and GFPm.

A study is initiated to evaluate if the integrated OsLEC1 transgene from these events will have any effect on the frequency of subsequent transformations. $T_1$ embryos from both OsLEC1 and control events are selected. Ears to be harvested are infused at 4DAP with compounds found to yield optimal embryogenic response for P38 [see U.S. Ser. No. 09/425,510 filed Oct. 22, 1999], harvested at 10DAP, and bombarded using the particle gun following the methodology listed in Example 2. The visual marker nos::CRC::pinII is used as the transgene for this study. CRC results in anthocyanin-accumulating events (i.e. red cells and tissues), and has been previously described (Bruce, W. et al., Plant Cell 12: 65-79, 2000). CRC expressing sectors are expected to be recovered at high frequencies without selective pressure across independent events only from the embryos segregating for the OsLEC1 transgene (based on GFPm expression). Wild type segregants as well as control events containing only the selectable marker and reporter gene are not expected to yield high frequencies of transformation. The data is expected to demonstrate that OsLEC1 expression improves transformation frequencies, and that this enhanced transformation is heritable.

What is claimed is:

1. A method for increasing LEC1 expression in a plant cell, wherein said increase is measured against a control plant cell, said method comprising introducing an isolated LEC1 nucleic acid into the plant cell to produce a plant cell that exhibits increased LEC1 expression, wherein the isolated LEC1 nucleic acid comprises a member selected from the group consisting of:
   (a) a polynucleotide which encodes a polypeptide of SEQ ID NO: 2;
   (b) a polynucleotide of SEQ ID NO: 1; and
   (c) a polynucleotide complementary to a polynucleotide of (a) or (b).

2. The method of claim 1 wherein the plant cell is stably transformed with the isolated LEC1 nucleic acid.

3. The method of claim 2 wherein the isolated LEC1 nucleic acid is operably linked to a promoter.

4. The method of claim 1 further comprising regenerating the plant cell to produce a plant.

5. The method of claim 1 where the plant cell is from a monocot plant or a dicot plant.

6. The method of claim 1 wherein the plant cell is from corn, soybean, sorghum, wheat, rice, alfalfa, sunflower, canola or cotton.

7. A plant produced by the method of claim 1.

* * * * *

SEQUENCE LISTING

<160> NUMBER OF SEQ ID NOS: 5

<210> SEQ ID NO 1
<211> LENGTH: 762
<212> TYPE: DNA
<213> ORGANISM: Oryza sativa
<220> FEATURE:
<221> NAME/KEY: CDS
<222> LOCATION: (1)...(762)

<400> SEQUENCE: 1

```
atg gag gcc ggc tac ccg ggc gcg gcg gcg aac ggc gct gcc gcc gac      48
Met Glu Ala Gly Tyr Pro Gly Ala Ala Ala Asn Gly Ala Ala Ala Asp
 1               5                  10                  15 ggg aac ggt ggc gcg cag cag gcg gcg gcc gcg ccg gct ata cgt gag      96
Gly Asn Gly Gly Ala Gln Gln Ala Ala Ala Ala Pro Ala Ile Arg Glu
             20                  25                  30 cag gac cgg ctg atg ccg atc gcg aac gtg atc cgc atc atg cgc cgc     144
Gln Asp Arg Leu Met Pro Ile Ala Asn Val Ile Arg Ile Met Arg Arg
         35                  40                  45 gtg ctc ccg gcg cac gcc aag atc tcg gac gac gcc aag gag acg atc     192
Val Leu Pro Ala His Ala Lys Ile Ser Asp Asp Ala Lys Glu Thr Ile
     50                  55                  60 cag gag tgc gtg tcg gag tac atc agc ttc atc acc ggg gag gcc aac     240
Gln Glu Cys Val Ser Glu Tyr Ile Ser Phe Ile Thr Gly Glu Ala Asn
 65                  70                  75                  80
```

```
gag cgg tgc cag cgc gag cag cgc aag acc atc acc gcc gag gac gtg      288
Glu Arg Cys Gln Arg Glu Gln Arg Lys Thr Ile Thr Ala Glu Asp Val
                85                  90                  95 ctc tgg gcc atg agc cgc ctc ggc ttc gac gac tac gtc gag ccc ctc      336
Leu Trp Ala Met Ser Arg Leu Gly Phe Asp Asp Tyr Val Glu Pro Leu
            100                 105                 110 ggc gtc tac ctc cac cgc tac cgc gag ttc gag ggg gag tcc cgc ggc      384
Gly Val Tyr Leu His Arg Tyr Arg Glu Phe Glu Gly Glu Ser Arg Gly
        115                 120                 125 gtc ggc gtc ggc gtc ggc gcc gcg cgc ggc gac cac cac cat ggt cac      432
Val Gly Val Gly Val Gly Ala Ala Arg Gly Asp His His His Gly His
130                 135                 140 gtc ggt ggg atg ctc aag tcc cgc gcg cag ggc tcc atg gtg acg cac      480
Val Gly Gly Met Leu Lys Ser Arg Ala Gln Gly Ser Met Val Thr His
145                 150                 155                 160 cac gac atg cag atg cac gcg gcc atg tac ggt ggc ggc gcg gtg ccg      528
His Asp Met Gln Met His Ala Ala Met Tyr Gly Gly Gly Ala Val Pro
                165                 170                 175 ccg ccg ccg cac cct cct ccg cac cac cac gcg ttc cac cag ctc atg      576
Pro Pro Pro His Pro Pro His His His Ala Phe His Gln Leu Met
            180                 185                 190 ccg ccg cac cac ggc cag tac gcg ccg ccg tac gac atg tac ggc ggc      624
Pro Pro His His Gly Gln Tyr Ala Pro Pro Tyr Asp Met Tyr Gly Gly
        195                 200                 205 gag cac ggg atg gcg gcg tac tac ggc ggg atg tac gcg ccc ggc agc      672
Glu His Gly Met Ala Ala Tyr Tyr Gly Gly Met Tyr Ala Pro Gly Ser
210                 215                 220 ggc ggc gac ggg agc ggc agc agc ggc agc ggt ggc gcc ggc acg ccg      720
Gly Gly Asp Gly Ser Gly Ser Ser Gly Ser Gly Gly Ala Gly Thr Pro
225                 230                 235                 240 cag acc gtc aac ttc gag cac cag cat ccg ttc gga tac aag              762
Gln Thr Val Asn Phe Glu His Gln His Pro Phe Gly Tyr Lys
                245                 250

<210> SEQ ID NO 2
<211> LENGTH: 254
<212> TYPE: PRT
<213> ORGANISM: Oryza sativa

<400> SEQUENCE: 2

Met Glu Ala Gly Tyr Pro Gly Ala Ala Ala Asn Gly Ala Ala Ala Asp
1               5                   10                  15

Gly Asn Gly Gly Ala Gln Gln Ala Ala Ala Pro Ala Ile Arg Glu
            20                  25                  30

Gln Asp Arg Leu Met Pro Ile Ala Asn Val Ile Arg Ile Met Arg Arg
        35                  40                  45

Val Leu Pro Ala His Ala Lys Ile Ser Asp Asp Ala Lys Glu Thr Ile
    50                  55                  60

Gln Glu Cys Val Ser Glu Tyr Ile Ser Phe Ile Thr Gly Glu Ala Asn
65                  70                  75                  80

Glu Arg Cys Gln Arg Glu Gln Arg Lys Thr Ile Thr Ala Glu Asp Val
                85                  90                  95

Leu Trp Ala Met Ser Arg Leu Gly Phe Asp Asp Tyr Val Glu Pro Leu
            100                 105                 110

Gly Val Tyr Leu His Arg Tyr Arg Glu Phe Glu Gly Glu Ser Arg Gly
        115                 120                 125

Val Gly Val Gly Val Gly Ala Ala Arg Gly Asp His His His Gly His
130                 135                 140
```

```
Val Gly Gly Met Leu Lys Ser Arg Ala Gln Gly Ser Met Val Thr His
145                 150                 155                 160

His Asp Met Gln Met His Ala Ala Met Tyr Gly Gly Gly Ala Val Pro
                165                 170                 175

Pro Pro Pro His Pro Pro His His Ala Phe His Gln Leu Met
            180             185                 190

Pro Pro His His Gly Gln Tyr Ala Pro Pro Tyr Asp Met Tyr Gly Gly
            195                 200                 205

Glu His Gly Met Ala Ala Tyr Tyr Gly Gly Met Tyr Ala Pro Gly Ser
        210                 215                 220

Gly Gly Asp Gly Ser Gly Ser Ser Gly Ser Gly Ala Gly Thr Pro
225             230                 235                 240

Gln Thr Val Asn Phe Glu His Gln His Pro Phe Gly Tyr Lys
                245                 250
```

<210> SEQ ID NO 3
<211> LENGTH: 65
<212> TYPE: PRT
<213> ORGANISM: Artificial Sequence
<220> FEATURE:
<223> OTHER INFORMATION: Lec1 amino acid consensus sequence
<220> FEATURE:
<221> NAME/KEY: VARIANT
<222> LOCATION: 5, 6, 18, 19, 22, 33, 45, 47, 51, 54, 55, 56, 57, 61,
      62, 63, 65
<223> OTHER INFORMATION: Xaa = Any Amino Acid

<400> SEQUENCE: 3

```
Arg Glu Gln Asp Xaa Xaa Met Pro Ile Ala Asn Val Ile Arg Ile Met
1               5                   10                  15

Arg Xaa Xaa Leu Pro Xaa His Ala Lys Ile Ser Asp Asp Ala Lys Glu
                20                  25                  30

Xaa Ile Gln Glu Cys Val Ser Glu Tyr Ile Ser Phe Xaa Thr Xaa Glu
            35                  40                  45

Ala Asn Xaa Arg Cys Xaa Xaa Xaa Xaa Arg Lys Thr Xaa Xaa Xaa Glu
    50                  55                  60

Xaa
65
```

<210> SEQ ID NO 4
<211> LENGTH: 25
<212> TYPE: DNA
<213> ORGANISM: Artificial Sequence
<220> FEATURE:
<221> NAME/KEY: primer_bind
<222> LOCATION: (1)...(25)
<223> OTHER INFORMATION: Primer
<220> FEATURE:
<223> OTHER INFORMATION: primer

<400> SEQUENCE: 4
atgcctctct acggctagct actcc                                        25

<210> SEQ ID NO 5
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: Primer
<220> FEATURE:
<223> OTHER INFORMATION: primer

```
<400> SEQUENCE: 5
cgccattctg ctgctgttac                                             20
```